(12) United States Patent
Puvanasunthararajah et al.

(10) Patent No.: US 12,277,627 B1
(45) Date of Patent: Apr. 15, 2025

(54) CORRECTION OF ULTRASOUND PROBE-INDUCED METAL ARTIFACTS IN X-RAY BASED IMAGING SYSTEMS

(71) Applicant: Queensland University of Technology, Brisbane (AU)

(72) Inventors: Sathyathas Puvanasunthararajah, Logan Central (AU); Saskia Camps, Prangins (CH); Davide Fontanarosa, Bulimba (AU); Adriano Garonna, Geneva (CH); Marie-Luise Wille, Jindalee (AU)

(73) Assignee: Queensland University of Technology, Brisbane (AU)

( * ) Notice: Subject to any disclaimer, the term of this patent is extended or adjusted under 35 U.S.C. 154(b) by 416 days.

(21) Appl. No.: 17/897,771

(22) Filed: Aug. 29, 2022

Related U.S. Application Data

(60) Provisional application No. 63/237,856, filed on Aug. 27, 2021.

(51) Int. Cl.
*G06T 11/00* (2006.01)
*A61B 6/00* (2024.01)
(Continued)

(52) U.S. Cl.
CPC ............ *G06T 11/008* (2013.01); *A61B 6/032* (2013.01); *A61B 6/4417* (2013.01);
(Continued)

(58) Field of Classification Search
CPC ............ G06T 11/008; G06T 2211/448; G06T 2211/421; G06T 2207/10081;
(Continued)

(56) References Cited

U.S. PATENT DOCUMENTS

| | | |
|---|---|---|
| 5,909,476 A | 6/1999 | Cheng et al. |
| 2006/0039591 A1 | 2/2006 | Zettel et al. |

(Continued)

FOREIGN PATENT DOCUMENTS

| | | |
|---|---|---|
| BE | 1024702 A1 | 5/2018 |
| CN | 103279929 A | 9/2013 |

(Continued)

OTHER PUBLICATIONS

Boas et al., Evaluation of Two Interative Techniques for Reducing Metal Artifacts in Computed Tomography, Radiology, vol. 259, No. 3, 9 pages, Jun. 2011.

(Continued)

*Primary Examiner* — Gandhi Thirugnanam
*Assistant Examiner* — Anna Lei
(74) *Attorney, Agent, or Firm* — Greenberg Traurig, LLP; Christopher C. Bolten; Robert D. Ward

(57) ABSTRACT

A metal artifact reduction (MAR) method and system for reducing metal artifacts from X-ray images. The method is suitable for CT images generated with metallic elements exterior to a patient being scanned, for example, where external probes are applied to a patient, such as ultrasound probes. The method may be embodied in a computer algorithm for use, for example, in radiotherapy treatment planning and patient positioning procedures. In one application, the disclosed technique improves the dose delivery accuracy in ultrasound-guided cardiac radioablation, making this treatment modality a viable option for cardiac arrhythmias.

20 Claims, 3 Drawing Sheets

(51) Int. Cl.
  *A61B 6/03* (2006.01)
  *A61B 34/20* (2016.01)
  *A61N 5/10* (2006.01)
(52) U.S. Cl.
  CPC .......... *A61B 6/5258* (2013.01); *A61B 34/20* (2016.02); *A61N 5/103* (2013.01); *G06T 2211/421* (2013.01)
(58) Field of Classification Search
  CPC ......... G06T 2207/10116; G06T 11/003; G06T 11/006; G06T 5/50; A61B 6/5258; A61B 6/032; A61B 6/4417; A61B 6/03; A61B 8/14; A61B 6/4085; A61B 34/20; A61B 2090/376; A61B 2090/3762; A61N 5/103; G06F 18/23; G06F 18/23213
  See application file for complete search history.

(56) References Cited

U.S. PATENT DOCUMENTS

| | | |
|---|---|---|
| 2009/0074278 A1 | 3/2009 | Beaulieu et al. |
| 2011/0038516 A1 | 2/2011 | Koehler et al. |
| 2013/0336450 A1 | 12/2013 | Kyriakou et al. |
| 2015/0004561 A1 | 1/2015 | Koehler |
| 2015/0092907 A1 | 4/2015 | Dong et al. |
| 2015/0146955 A1 | 5/2015 | Dong et al. |
| 2015/0371420 A1 | 12/2015 | Yerushalmy et al. |
| 2016/0117850 A1 | 4/2016 | Jin et al. |
| 2016/0125625 A1 | 5/2016 | Kim et al. |
| 2016/0324499 A1 | 11/2016 | Sen Sharma et al. |
| 2016/0371862 A1 | 12/2016 | Silver et al. |
| 2018/0350113 A1* | 12/2018 | Goto ................ A61B 6/5258 |
| 2019/0164288 A1 | 5/2019 | Wang et al. |
| 2019/0380670 A1 | 12/2019 | Hofmann et al. |
| 2020/0000417 A1* | 1/2020 | Durzinsky ........... G06T 11/006 |
| 2020/0151921 A1 | 5/2020 | Schildkraut |
| 2021/0012544 A1 | 1/2021 | Lee et al. |
| 2021/0065414 A1 | 3/2021 | Do |

FOREIGN PATENT DOCUMENTS

| | | | |
|---|---|---|---|
| CN | 107730455 A | 2/2018 | |
| CN | 108022272 A | 5/2018 | |
| CN | 111223156 A | 6/2020 | |
| DE | 102014217966 A1 | 3/2016 | |
| EP | 3628230 A1 * | 4/2020 | ............ A61B 6/032 |
| FR | 3058249 A3 | 5/2018 | |
| KR | 1020110040164 A | 4/2011 | |
| WO | 2013/129811 A1 | 9/2013 | |
| WO | 2019/017752 A1 | 1/2019 | |
| WO | 2019/096943 A1 | 5/2019 | |
| WO | 2020/033355 A1 | 2/2020 | |
| WO | 2020/075106 A2 | 4/2020 | |
| WO | 2020/142397 A1 | 7/2020 | |
| WO | 2020/212573 A1 | 10/2020 | |
| WO | 2021/094824 A1 | 5/2021 | |
| WO | 2022/136925 A1 | 6/2022 | |

OTHER PUBLICATIONS

Koike et al., Dee learning-based metal artifact reduction using cycle-consistent adversarial network for intensity-modulated head and neck radiation therapy treatment planning, Physica Medica, 78, 7 pages, 2020.

Luzhbin et al., Model Image-Based Metal Artifact Reduction for Computed Tomography, Journal of Digital Imaging 33, 12 pages, 2020.

Nakao et al., Regularized Three-Dimensional Generative Adversarial Nets for Unsupervised Metal Artifact Reduction in Head and Neck CT Images, Digital Object Identifier, vol. 8, 13 pages, 2020.

Schlosser et al., Radiolucent 4D Ultrasound Imaging: System Design and Application to Radiotherapy Guidance, Transactions of Medical Imaging, vol. 35, No. 10, 9 pages, Oct. 2016.

Wellenberg et al., Metal artifact reduction techniques in musculo-skeletal CT-Imaging, European Journal of Radiology, 107, 10 pages, 2018.

* cited by examiner

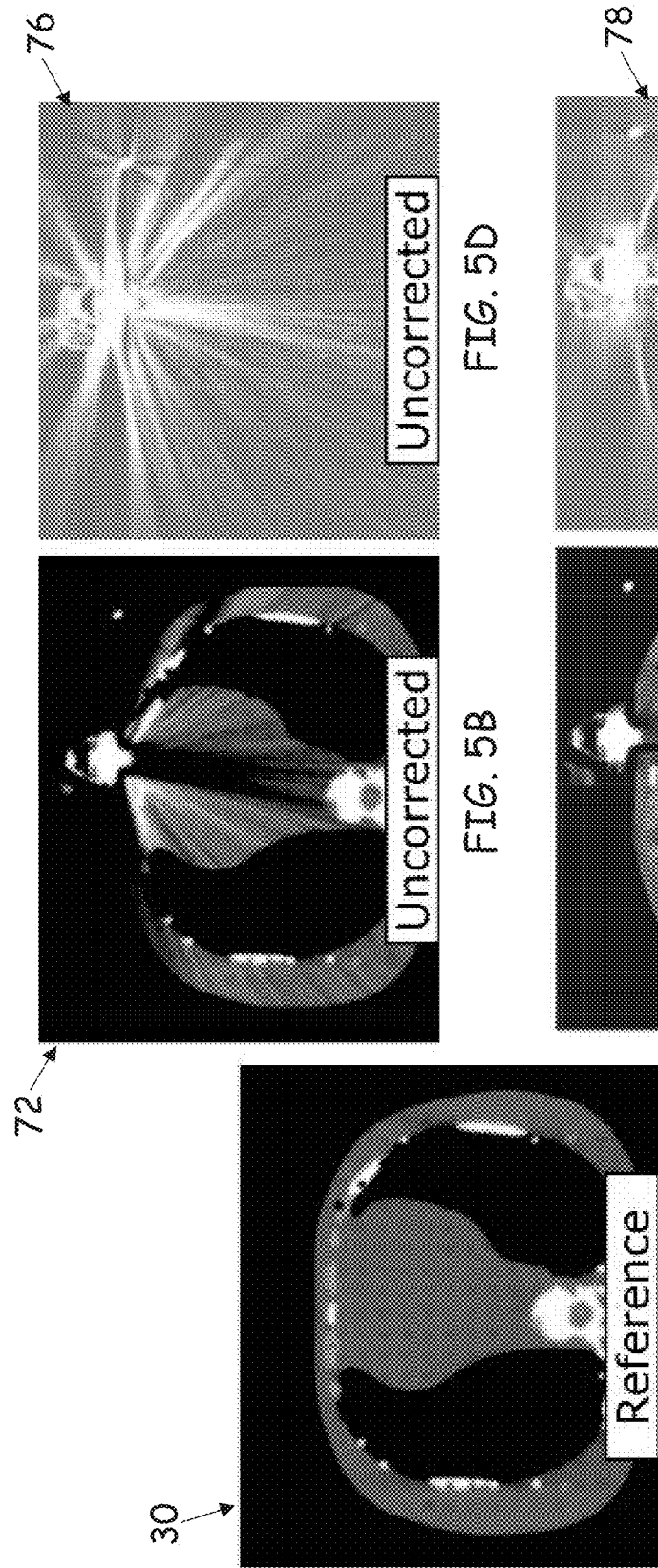

CORRECTION OF ULTRASOUND PROBE-INDUCED METAL ARTIFACTS IN X-RAY BASED IMAGING SYSTEMS

RELATED APPLICATIONS

This patent application claims the benefit of U.S. Provisional Application No. 63/237,856, filed Aug. 27, 2021, the disclosure of which is hereby incorporated by reference herein in its entirety.

FIELD OF THE DISCLOSURE

This application is directed generally to the simultaneous acquisition of ultrasound and X-ray based images and more specifically to correction of metal artifacts on X-ray images.

BACKGROUND

Radiation therapy is a treatment option for several types of cancer and more recently for treatment of cardiac arrhythmias. The aim of this treatment is to irradiate the target, while sparing the surrounding normal tissue as much as possible. Ultrasound imaging can provide guidance during radiation therapy workflows for depositing radiation doses at a desired location. During a typical radiation therapy workflow, X-ray based imaging is used in several steps. For example, during the simulation stage a computed tomography (CT) scan is acquired based on which a treatment plan is prepared. During treatment, patient alignment can be done, for example, based on double X-ray or cone-beam CT (CBCT) imaging.

Cardiac radioablation has emerged as a promising treatment for cardiac arrhythmias. However, accurate dose delivery can be affected by motion of the heart. Ultrasound imaging can offer real-time cardiac motion monitoring during the ablation, but requires simultaneous imaging of ultrasound and planning CT, which can result in ultrasound transducer induced metal artifacts on the planning CT scans.

Metal artifacts can severely compromise the quality of an X-ray image, which can result, for example, in a sub-optimal treatment plan or an inaccurate patient alignment. While metal artifact reduction (MAR) algorithms exist that effectively reduce the metal artifacts through digital manipulation of the images, such conventional MAR algorithms do not satisfactorily reduce metal artifacts in the X-ray images where ultrasound probes are present. There is a need for a system and technique that corrects for metal artifacts generated by ultrasound probes.

SUMMARY OF THE DISCLOSURE

Various embodiments of the disclosure are directed to correction of metal artifacts generated by the presence of ultrasound probes externally mounted to a subject being X-rayed. The reduction of the metal artifacts appearing on X-ray images may be accomplished without the need to change the characteristics of the ultrasound probe itself. Also, the method is robust and can be implemented for ultrasound probes of different models with little or no need for alteration of the method. Reduction of the metal artifacts enhances X-ray image quality of systems implementing ultrasound probes (and more generally of artifacts generated by any device externally mounted to the subject). Accordingly, the disclosed methods and systems constitute an improvement to the functionality of computer based methods and systems that control the acquisition of such X-ray images and technologically advances the X-ray imaging field.

In some embodiments, the method makes use of reconstructed CT scans instead of using sinogram data. Sinogram data are typically saved in a proprietary file format that is specific to a given CT scanner vendor and sometimes even specific to individual CT scanners. Often, the proprietary file formats cannot be exported or otherwise viewed by third parties. Accordingly, some embodiments of the disclosed method and system use reconstructed CT scans as the starting point, thereby making the algorithm CT scanner applicable to all vendors. Alternatively, collaboration with CT scanner vendors is also contemplated, for access to proprietary file formats and reduction of probe specific artifacts using the sinograms.

Successful reduction of metal artifacts resulting from the ultrasound probe enables use of the ultrasound probe during imaging in the radiation therapy workflow while reducing, for example, negative effects on the final treatment plan quality or patient alignment accuracy. Furthermore, even where imaging modalities are not used strictly simultaneously, there is still the benefit that no anatomical changes will occur between both image modalities due to removal/positioning of the ultrasound probe. In some applications, a reduction of the metal artifacts will enable simultaneous imaging by ultrasound imaging and an X-ray based image modality for improved spatial and time correlation of the data that is captured by both image modalities. This can lead to better diagnostics for organs where X-ray based and ultrasound based imaging give complementary information.

Conventional MAR algorithms, both commercial and research-based, are designed primarily for the metal artifacts created by metal components that are implanted inside the body of the patient. Examples of MAR-appropriate applications include metal hip replacements, bone screws, and dental implants. However, ultrasound probes, being placed externally on the thorax of the patient, produce artifacts in fewer directions than do implanted metal components, thereby producing fundamentally different artifact patterns.

In addition to CT scans, the same phenomena are observed for all X-ray based imaging systems, such as cone-beam CT (CBCT) and double X-ray, which are typically used to align the patient prior to a radiation therapy treatment. As these other X-ray image modalities also can play a role in radiation therapy workflows, they should also be taken into account. More generally, the phenomena occurs when a metallic material external to the patient is present in the X-ray image, for example with an ultrasound probe (as discussed) or external defibrillator/pacemaker on the chest, or a deep brain stimulation device. The techniques disclosed herein may also be useful for intra-treatment imaging, including the use of ultrasound probes for guidance of surgical tools together with other X-ray based modalities, enabling correction of metal artifacts on the images where the probe is in the operation field, thereby improving tool guidance accuracy or robot precision in case of robotic surgery. Another possible application is for angiographic suites, where guidance of catheter insertion uses a combination of X-rays and ultrasound is contemplated.

For the present disclosure, example CT scans from an anthropomorphic phantom with ultrasound transducer induced artifacts were used. Initially, metal data are segmented from the original CT scan. Using multi-threshold segmentation on the original CT scan, two clustered digital objects are created and combined. Forward projections of the metal data, the original CT scan, and the combined clustered digital objects result in a metal-only sinogram, an original sinogram, and a clustered sinogram. The original sinogram is divided by the clustered sinogram and masked using the metal-only sinogram for the interpolation. The outcome is multiplied by the clustered sinogram. A final CT scan is reconstructed by filtered-back projection. To demonstrate the effectiveness of the disclosed technique, Hounsfield Units on the original CT scan and the corrected CT scan are compared with a reference CT scan from the anthropomorphic phantom that was taken without the ultrasound transducer present.

Structurally, various embodiments of the disclosure include a method for correcting metal artifacts in an X-ray image, comprising some or all of the following: obtaining an original digital object corresponding to an X-ray image; identifying metal data within the original digital object to define a metal-only digital object; generating a first tissue classified digital object from the original digital object; incorporating a spatial relationship among adjacent pixels of the original digital object; generating a metal-only sinogram from the metal-only digital object; generating a first tissue classified sinogram from the first tissue classified digital object; generating an original sinogram from the original digital object; dilating and smoothing the metal-only sinogram; after dilating and smoothing the metal-only sinogram, combining the metal-only sinogram, the first tissue classified sinogram, and the metal-only sinogram to create an initial metal artifact reduction (MAR) digital object; calculating differences of represented weighted linear attenuation coefficients between corresponding pixels of the original digital object and the initial MAR digital object; identifying pixels having the differences that are within a predetermined range; designating the pixels identified in the step of identifying pixels as soft tissue on the initial MAR digital object; generating a second tissue classified digital object from the MAR digital object; generating a combined tissue classified digital object from the first tissue classified digital object and the second tissue classified digital object; calculating mean absolute differences between corresponding pixels the first tissue classified digital object and the second tissue classified digital object; adding the mean absolute differences with the first tissue classified digital object; and generating a combined sinogram from the combined tissue classified digital object.

In some embodiments, the step of identifying the metal data from the original digital object includes a thresholding based on the Hounsfield Units. The step of generating at least one of the first tissue classified digital object and the second tissue classified digital object may highlight air, bone, and soft tissue pixels. In some embodiments, at least one of the steps of generating the first tissue classified digital object and generating the second tissue classified digital object includes a k-means clustering operation with a plurality (e.g., three) clusters. The step of incorporating the spatial relationship may include a filtering operation. In some embodiments, the step of generating the metal-only sinogram includes forward projecting the metal-only digital object. The step of generating the tissue classified sinogram may include forward projecting the tissue classified digital object. In some embodiments, the step of generating the original sinogram includes forward projecting the original digital object. The step of dilating and smoothing the metal-only sinogram may include using morphological operations and Gaussian filters. In some embodiments, the data identified in the step of identifying metal data is associated with an ultrasound probe. Various embodiments of the disclosure may further comprise acquiring an ultrasound image with the ultrasound probe simultaneously with the step of obtaining the original digital object. In some embodiments, the step of calculating the mean absolute differences is performed during the step of generating the combined tissue classified digital object. The original digital object obtained during the step of obtaining the original digital object may be from a computed tomography (CT) scan.

In various embodiments of the disclosure, the method is actualized by a module on a computer-readable, non-transitory medium configured with computer-readable instructions that execute the method. In some embodiments, the method is actualized by a computer- or processor-controlled system. The system may include X-ray and ultrasound imaging devices and control the acquisition of images therefrom.

BRIEF DESCRIPTION OF THE DRAWINGS

FIG. 5A is a CT scan acquired without an ultrasound probe present during the imaging;

FIG. 5B is an uncorrected CT scan a with an ultrasound probe in place during the imaging;

FIG. 5C is a corrected CT scan of FIG. 5B according to an embodiment of the disclosure;

FIG. 5D depicts an absolute difference in pixel values between the reference CT scan of FIG. 5A and the uncorrected CT scan of FIG. 5B according to an embodiment of the disclosure; and FIG. 5E depicts an absolute difference in pixel values between the reference CT scan of FIG. 5A and the corrected CT scan of FIG. 5C according to an embodiment of the disclosure.

DETAILED DESCRIPTION OF THE DRAWINGS

Figures 1, 2, 3:
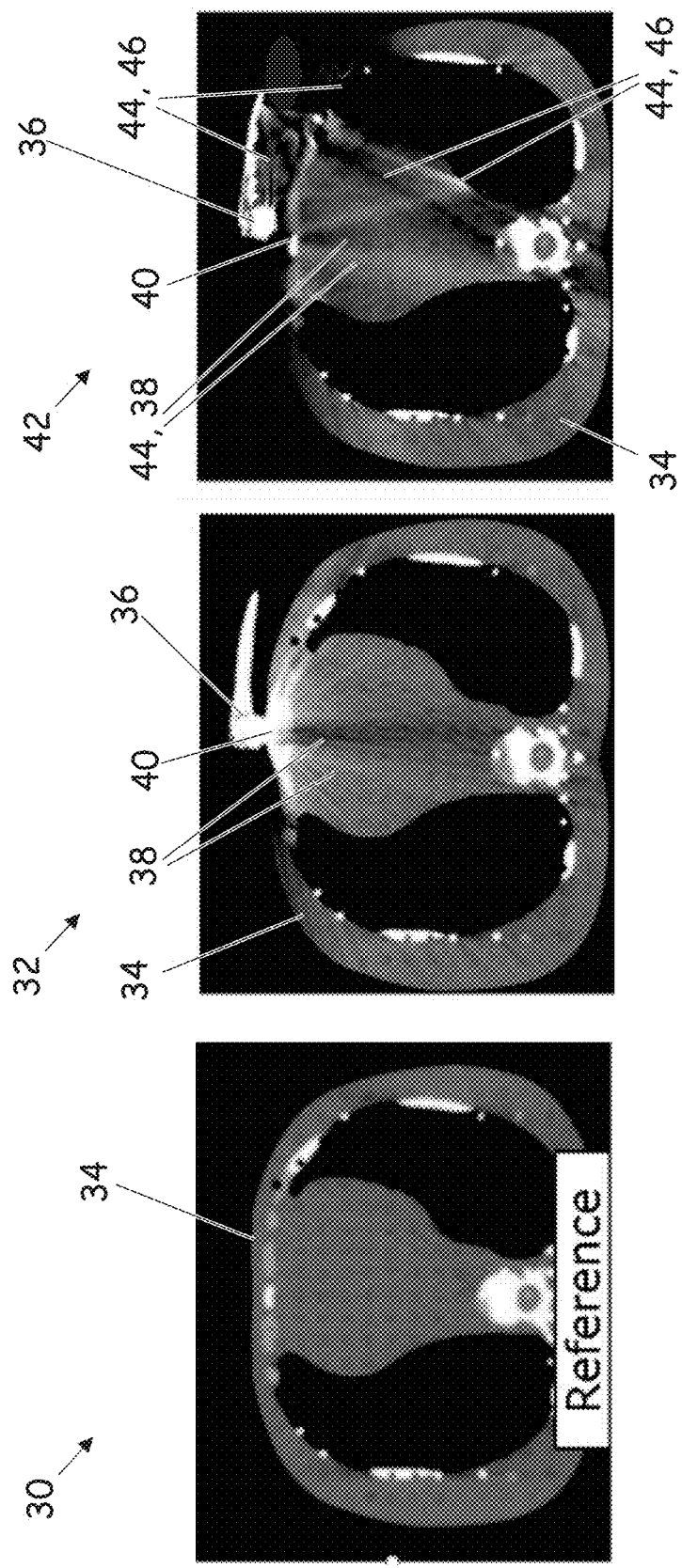
FIG. 1 is a CT scan acquired without an ultrasound probe present during the imaging.
FIG. 2 is a CT scan acquired as in FIG. 1 but with an ultrasound probe present during the imaging.
FIG. 3 is the CT scan of FIG. 2 after application of a conventional metal artifact correction algorithm.

Referring to FIGS. 1 and 2, CT scan images 30 and 32 of an anthropomorphic phantom 34 acquired respectively without and with an ultrasound probe 36 present during the imaging are depicted. The anthropomorphic phantom 34 is made of materials with characteristics similar to normal biological organisms for simulating a subject, such as a human patient or an animal. The ultrasound probe 36 contains metal components and therefore its presence in the X-ray beam during imaging can cause metal artifacts 38 on the resulting X-ray imaging. Herein, a "metal artifact" is something observed in an X-ray that is not naturally present but occurs as a result of metal in the X-ray field. Such metal artifacts 38 may be characterized, for example, by dark and bright spots and/or streaks in the X-ray image which may obscure and degrade the quality of the image 32.

The degree of obscurity and image degradation caused by metal artifacts is well documented. Examples include Schlosser et al., "Radiolucent 4D Ultrasound Imaging: System Design and Application to Radiotherapy Guidance," *IEEE Trans. Med. Imaging* vol. 35., pp. 2292-2300 (2016) (herein "Schlosser et al.") and Wellenberg et al., "Metal artifact reduction techniques in musculoskeletal CT-imaging," *European Journal of Radiology* vol. 107, pp. 60-69 (2018), both incorporated by reference herein.

Conventionally, to avoid metal artifacts 38 where both X-ray imaging and ultrasound imaging are needed, the images are acquired sequentially instead of simultaneously, requiring either removal of the ultrasound probe 36 before X-ray imaging or placement of the ultrasound probe 36 immediately after the X-ray imaging. The sequential acquisition necessitates that the X-ray and ultrasound image modalities be acquired at different points in time. Such asynchronous acquisition of the images can be problematic, particularly for anatomical structures that undergo substantial movement between acquisitions (e.g., due to respiratory or heartbeat motion). In addition, the placement or removal of the ultrasound probe 36 can deform the skin layers due to pressure changes that occur at a placement site 40 of the ultrasound probe 36, thereby also deforming the underlying anatomical structures. As such, even when the anatomical structures do not undergo substantial movement, the orientation, shape, and location of anatomical structures proximate the placement site 40 of the ultrasound probe 36 can be altered between the images acquired with and without the ultrasound probe 36. To make better use of the capabilities that ultrasound imaging has to offer, simultaneous acquisition of both the X-ray and the ultrasound image modalities is desired, with attendant reduction or elimination of metal artifacts.

Attempts have been made to produce an ultrasound probe with fewer metal components, in hopes of adequately reducing the metal artifacts (see, e.g., Schlosser et al.). However, cases where such probes can be implemented are limited and the resultant ultrasound images are generally substandard.

Metal artifact reduction (MAR) algorithms exist, both commercially and research-based, that reduce metal artifacts created by metal implants. Examples of commercial MAR algorithms include the O-MAR by Philips Health System of Cleveland, Ohio, USA, the IMAR® by Siemens Healthcare of Forchheim, Germany, the SMART MAR by General Electric Healthcare of Chicago, Illinois, USA, and the SEMAR® by Canon/Toshiba Medical Systems of Otawara, Japan. Examples of research-based algorithms are found, for example, at Boas et al., "Evaluation of two iterative techniques for reducing metal artifacts in computed tomography", *Radiology* 259, 894-902 (2011) and Luzhbin, et al., "Model Image-Based Metal Artifact Reduction for Computed Tomography", *Journal of Digital Imaging* 33, 71-82 (2020).

Referring again to FIG. 2 and to FIG. 3, CT scan images 32 and 42 with the uncorrected metal artifacts 38 and post-MAR corrected artifacts 44, respectively, are depicted. The post-MAR artifacts 44 were generated by processing the uncorrected image 32 with a conventional MAR technique. For the post-MAR image 42, not only do certain metal artifacts 38 from the uncorrected image 32 remain in the corrected artifacts 44, but additional processing artifacts 46 are introduced, as identified on the post-MAR image 42. While the post-MAR image 42 was obtained using the O-MAR system, the same issues exist with conventional MAR algorithms generally. Accordingly, for an externally positioned ultrasound probe, substantial residual traces from the metal artifacts 38 may remain after processing with conventional MAR algorithms, and processing artifacts 46 may be created on the post-MAR image 42.

Figure 4:
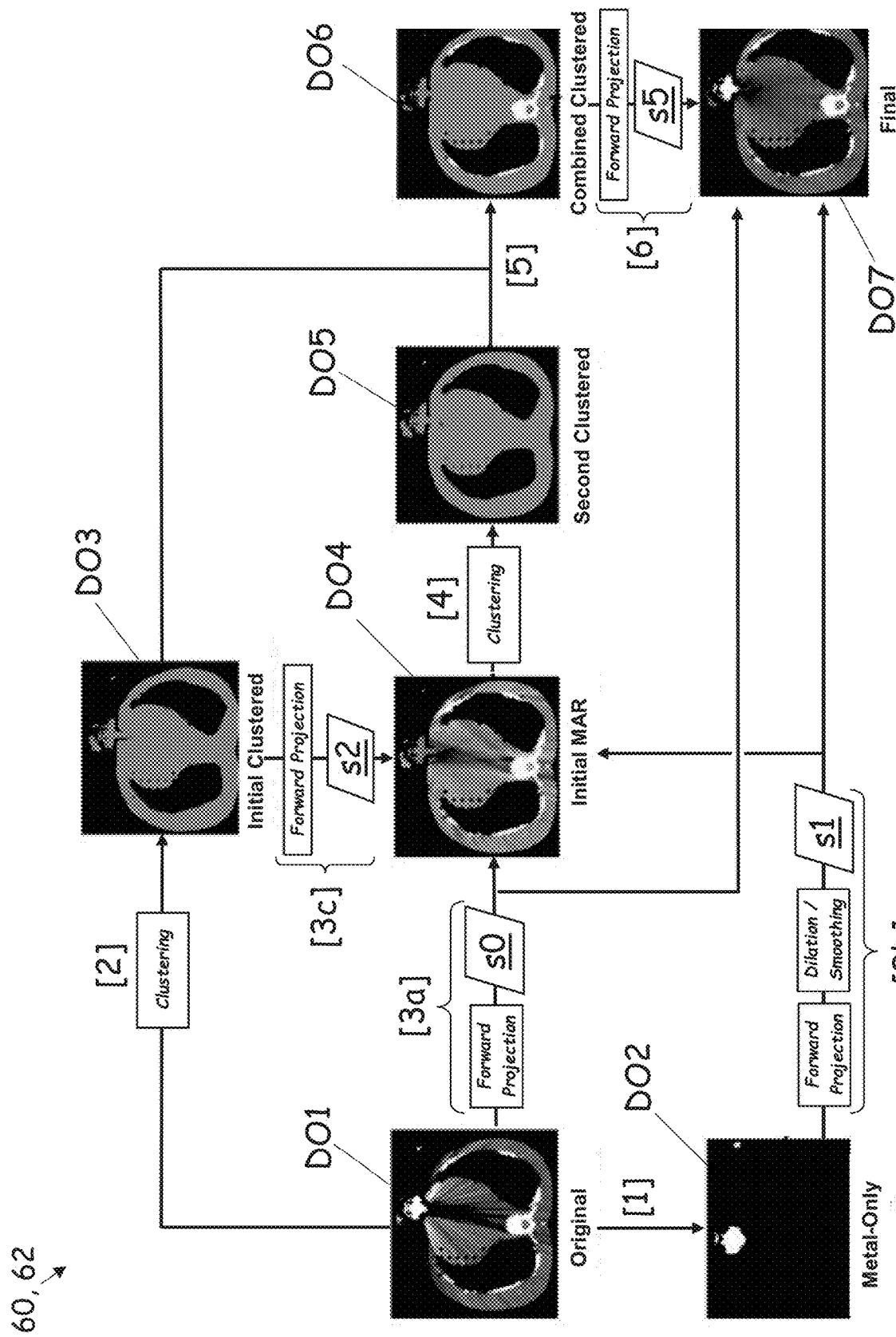
FIG. 4 is a diagram of a work flow for an external probe MAR method according to an embodiment of the disclosure.

Referring to FIG. 4, an illustrated workflow diagram 60 depicting an external probe MAR method 62 for reducing the metal artifacts 38 on the CT scan image 32 is depicted according to an embodiment of the disclosure. The workflow diagram 60 includes icons representing digital objects Doi, where i is a numerical suffix that identifies the specific digital object DO of a given step of the external probe MAR method 62. The digital objects DOi may be realized during the external probe MAR method 62, as well as attendant method steps (indicated in square brackets on the workflow diagram 60) that are applied to the various digital objects Doi.

An original digital object DO1 is generated by a CT scan. Raw data generated by a CT scanner are referred to herein as "sinograms," which are subsequently used to reconstruct a CT image that can be interpreted, for example, by radiologists. There is no standard format for sinogram data. Instead, sinogram data is typically vendor- and CT-scanner specific, and often not available to third parties. Accordingly, the "original" digital object DO1 generated by a CT scan may be sinogram data or reconstructed data provided by the CT scanner.

The external probe MAR method 62 may include generation of a metal-only digital object DO2 (step [1]). The metal-only digital object DO2 identifies and isolates data within the original digital object DO1 that correlates with the presence of metallic material. The identification may be accomplished by metal segmentation. In some embodiments, the metal segmentation involves subjecting the original digital object DO1 to a thresholding based on the Hounsfield Units (HU), enabling the identification of the pixels that indicate the presence of metal in the original digital object DO1.

In some embodiments, the external probe MAR method 62 generates an initial clustered digital object DO3 (step [2]). A k-means clustering operation with a plurality of clusters may be performed at step [2], resulting in the generation of a tissue classified scan highlighting pixels that are indicative of air, bone and soft tissue. In some embodiments, the plurality of clusters is three clusters. Adjacent pixels in CT scans are typically highly correlated and contain similar features. Because of the presence of the metal artifacts, the air, bone, and soft tissue pixels are prone to misclassification in different clusters. Accordingly, step [2] may include a filtering operation to incorporate a spatial relationship among adjacent pixels, which may prevent such misclassification.

An initial MAR digital object DO4 may be generated from the original digital object DO1, the metal-only digital object DO2, and the initial clustered digital object DO3. In some embodiments, each of the digital objects DO1, DO2, and DO3 may be forward projected to generate respective sinograms s0, s1, and s2 (steps [3a], [3b], and [3c]). In some embodiments, the metal-only sinogram s1 is also dilated and smoothed at step [3a], for example with morphological operations and gaussian filters. In some embodiments, the initial MAR digital object DO4 may be generated from sinograms of s0, s1, and s2 after dilation and smoothing of sinogram s1. In some embodiments, the initial MAR digital object DO4 is created based on the method of Meyer et al., "Normalized metal artifact reduction (NMAR) in computed tomography," Med. Phys. 37 5482-5493 (2010).

To further reduce the metal artifacts, the initial MAR digital object DO4 may be clustered again following the same procedure as described for step [2] for generation of a second clustered digital object DO5. Prior to step [4], pixel-wise differences between the original digital object DO1 and the initial MAR digital object DO4 may be calculated. A predetermined HU value range may be selected to identify the corresponding pixels which have HU values in the calculated difference. The HU values of such identified pixels may be designated as soft tissue. In some embodiments, the predetermined HU value range is from 200 HU to 400 HU inclusive. Herein, a range that is said to be "inclusive" includes the endpoint values of the stated range.

The digital objects DO3 and DO5 resulting from steps [2] and [4] may then be combined to produce a combined clustered digital object DO6 (step [5]). During step [5], a mean absolute difference between the initial and second clustered digital objects DO3 and DO5 may be calculated and added with the initial clustered digital object DO3. In some embodiments, the combined clustered digital object DO6 is forward projected to generate a sinogram s5 (step [6]). Sinogram s5 may be combined with sinograms s0 and s1 to generate the final digital object DO7, which may be rendered as an image. Combination of sinograms s0, s1, and s6 may be performed, for example, based on the method described by Meyer et al.

Referring to FIGS. 5A through 5E, the effect of the above-described external probe MAR method 62 is depicted according to embodiments of the disclosure. The CT scan image 30 (without an ultrasound probe in place) is included at FIG. 5A as a reference condition that represents an aspirational CT scan image that has no metal artifacts. The FIGS. 5B and 5C depict an uncorrected CT scan image 72 with the ultrasound probe 36 in place and a corrected CT scan image 74 corrected according to the external probe MAR method 62. An uncorrected differential map 76 presents the absolute differences between pixel values of the uncorrected CT scan image 72 and the reference CT scan image 30 (FIG. 5D). Likewise, a corrected differential map 78 presents the absolute differences between the corrected CT and the reference scan images 74 and 30 (FIG. 5E).

The absolute differences of the uncorrected and corrected differential maps 76 and 78 are presented with proportional brightness. That is, areas of greater difference with respect to the reference CT scan image 30 are depicted with greater brightness. Both of the uncorrected and corrected differential maps 76 and 78 necessarily indicate large absolute differences at the pixels that image the ultrasound probe 36, which is absent in the reference CT scan image 30. The differential map 76 for the uncorrected CT scan image 72 depicts bright streaks of high absolute difference emanating from the region of the ultrasound probe 36 that correlate with the errantly bright and dark pixels that are characteristic of metal artifacts. For the differential map 78 of the corrected CT scan image 74, the streaks The differential map 78, as well as visual inspection of CT scan images 74 and 30, demonstrates that there are fewer differences between the aspirational reference CT scan image 30 and the corrected scan image 74 than there are between the reference and the uncorrected scan images 30 and 72. As such, the external probe MAR method 62 substantially removes metal artifacts of X-rays taken in the presence of an external probe. Also, visual comparison of corrected CT scan image 74 with the post-MAR image 42 (FIG. 3) reveals the external probe MAR method 62 has substantially fewer residual traces than those left by the conventional MAR algorithms, and that the additional processing artifacts 46 characteristic of conventional MAR algorithms are largely absent or substantially diminished for the external probe MAR method 62, particularly in the interior regions of the CT scan images.

The use of deep learning techniques are also contemplated for reduction of metal artifacts. Deep learning algorithms for correcting metal artifacts induced by metal implants are disclosed, for example, by Koike et al., "Deep learning-based metal artifact reduction using cycle-consistent adversarial network for intensity-modulated head and neck radiation therapy treatment planning," Phys. Medica. 78 8-14 (2020). While the foregoing primarily discusses systems using CT scanner imaging, the phenomena discussed can be observed generally for all X-ray based imaging systems, including but not limited to cone-beam CT (CBCT) and double X-ray. As such, the discussions of CT scanners and CT images are by way of example only and are non-limiting.

In some embodiments, the external probe MAR method is actualized on a computer-readable, non-transitory medium or system configured with computer-readable instructions for executing the method. Non-limiting examples of a computer-readable, non-transitory medium include compact discs and magnetic storage devices (e.g., hard disk, flash drive, cartridge, floppy drive). The computer-readable media may be local or accessible over the internet. The computer-readable instructions may be complete on a single medium, or divided among two or more media The following references are incorporated by reference herein in their entirety except for patent claims and express definitions contained therein: Schlosser et al., "Radiolucent 4D Ultrasound Imaging: System Design and Application to Radiotherapy Guidance," *IEEE Trans. Med.* Imaging vol. 35., pp. 2292-2300 (2016); Boas et al., "Evaluation of two iterative techniques for reducing metal artifacts in computed tomography," *Radiology* vol. 259, pp. 894-902 (2011); Luzhbin et al., "Model Image-Based Metal Artifact Reduction for Computed Tomography," *Journal of Digital Imaging* vol. 33, pp. 71-82 (2020); Wellenberg et al., "Metal artifact reduction techniques in musculoskeletal CT-imaging," *European Journal of Radiology* vol. 107, pp. 60-69 (2018); Meyer et al., "Normalized metal artifact reduction (NMAR) in computed tomography," *Med. Phys.* vol. 37, pp. 5482-5493 (2010); Koike et al., "Deep learning-based metal artifact reduction using cycle-consistent adversarial network for intensity-modulated head and neck radiation therapy treatment planning," *Phys. Medica* vol. 78, pp. 8-14 (2020); Nakao et al., "Regularized three-dimensional generative adversarial nets for unsupervised metal artifact reduction in head and neck CT images," *IEEE Access* vol. 8, pp. 109453-465 (2020); International Patent Application Publication No. WO 2019/096943 to Garonna et al., filed 15 Nov. 2018; International Patent Application Publication No. WO 2021/094824 to Camps et al., filed Nov. 11, 2020; International Patent Application Publication No. WO 2020/075106 to Sauli et al., filed Oct. 10, 2019; U.S. Provisional Patent Application No. to Camps et al., 63/129,694, filed Dec. 23, 2020.

Any incorporation by reference of documents above is limited such that no subject matter is incorporated that is contrary to the explicit disclosure herein. Any incorporation by reference of documents above is further limited such that no patent claims included in the documents are incorporated by reference herein. Any incorporation by reference of documents above is yet further limited such that any definitions provided in the documents are not incorporated by reference herein unless expressly included herein.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize, in view of this disclosure, that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A system for correcting metal artifacts in an X-ray image of a subject, said system comprising:
    a processor configured to:
        obtain an original digital object corresponding to an original X-ray image with an X-ray based imaging system;
        identify, within said original digital object, metal data associated with a device externally mounted to said subject to define a metal-only digital object;
        generate a first tissue classified digital object from said original digital object;
        incorporate a spatial relationship among adjacent pixels of said original digital object;
        generate a metal-only sinogram from said metal-only digital object;
        generate a first tissue classified sinogram from said first tissue classified digital object;
        generate an original sinogram from said original digital object;
        dilate and smooth said metal-only sinogram;
        combine said metal-only sinogram, said first tissue classified sinogram, and said original sinogram to create an initial metal artifact reduction (MAR) digital object;
        calculate differences of represented weighted linear attenuation coefficients between corresponding pixels of said original digital object and said initial MAR digital object;
        identify pixels having said differences that are within a predetermined range;
        designate said pixels identified in the step of identifying pixels as soft tissue on said initial MAR digital object;
        generate a second tissue classified digital object from said MAR digital object;
        generate a combined tissue classified digital object from said first tissue classified digital object and said second tissue classified digital object;
        calculate mean absolute differences between corresponding pixels of said first tissue classified digital object and said second tissue classified digital object;
        add said mean absolute differences with said first tissue classified digital object; and
        generate a combined sinogram from said combined tissue classified digital object.

2. The system of claim 1, wherein said processor is configured to threshold based on Hounsfield Units to identify said metal data from said original digital object.

3. The system of claim 1, wherein said processor is configured to highlight air, bone, and soft tissue pixels to generate at least one of said first tissue classified digital object and said second tissue classified digital object.

4. The system of claim 1, wherein said processor is configured to perform a k-means clustering operation with a plurality of clusters to generate at least one of said first tissue classified digital object and said second tissue classified digital object.

5. The system of claim 1, wherein said processor is configured for a filtering operation to incorporate said spatial relationship.

6. The system of claim 1, wherein said processor is configured to forward project said metal-only digital object to generate said metal-only sinogram.

7. The system of claim 1, wherein said processor is configured to forward project said tissue classified digital object to generate said first tissue classified sinogram.

8. The system of claim 1, wherein the said processor is configured to forward project said original digital object to generate said original sinogram.

9. The system of claim 1, wherein said processor is configured for morphological operations and gaussian filters to dilate and smooth said metal-only sinogram.

10. The system of claim 1, wherein said processor is configured to simultaneously generate said combined tissue classified digital object and calculate said mean absolute differences.

11. The system of claim 1, wherein said processor is configured to identify metal data associated with an ultrasound probe.

12. The system of claim 11, wherein said X-ray based imaging system is a computed tomography (CT) scanner.

13. The system of claim 12, comprising said CT scanner.

14. The system of claim 1, wherein said device externally mounted to said subject is an ultrasound probe.

15. The system of claim 14, wherein said processor is configured to obtain an ultrasound image generated by said ultrasound probe and to obtain said original digital object simultaneously.

16. The system of claim 15 comprising said ultrasound probe.

17. The system of claim 1, wherein said device externally mounted to said subject is one of a defibrillator, a pacemaker, and a deep brain stimulation device.

18. The system of claim 17, comprising said one of a defibrillator, a pacemaker, and a deep brain stimulation device.

19. The system of claim 1, wherein said processor is configured to resolve an image for cardiac radioablation.

20. The system of claim 1, wherein said processor is configured to resolve an image for guidance of a catheter for an angiographic suite.

* * * * *